(12) United States Patent
Commo

(10) Patent No.: US 8,481,762 B2
(45) Date of Patent: Jul. 9, 2013

(54) ADMINISTRATION OF COMPOUNDS THAT INCREASE GLUTATHIONE LEVELS IN THE MELANOCYTES FOR THE TREATMENT OF CANITIES

(75) Inventor: Stephane Commo, Chaville (FR)

(73) Assignee: L'Oreal, Paris (FR)

( * ) Notice: Subject to any disclaimer, the term of this patent is extended or adjusted under 35 U.S.C. 154(b) by 273 days.

(21) Appl. No.: 11/812,900

(22) Filed: Jun. 22, 2007

(65) Prior Publication Data

US 2008/0014229 A1    Jan. 17, 2008

Related U.S. Application Data

(63) Continuation of application No. PCT/FR2005/003196, filed on Dec. 20, 2005.

(30) Foreign Application Priority Data

Dec. 22, 2004 (FR) .................................... 04 13756

(51) Int. Cl.
*C07D 307/77* (2006.01)
*A61K 9/50* (2006.01)

(52) U.S. Cl.
USPC .......... 549/456; 424/490; 424/70.1; 514/880; 514/852

(58) Field of Classification Search
USPC ........... 514/880, 852; 424/70.1, 490; 549/456
See application file for complete search history.

(56) References Cited

U.S. PATENT DOCUMENTS

| | | | | |
|---|---|---|---|---|
| 4,793,990 A | * | 12/1988 | Grollier et al. .................. | 424/59 |
| 5,516,507 A | | 5/1996 | N'Guyen et al. | |
| 5,928,654 A | * | 7/1999 | Duranton ....................... | 424/401 |
| 6,103,689 A | * | 8/2000 | Gilchrest et al. ................. | 514/2 |
| 6,110,474 A | * | 8/2000 | Roman ......................... | 424/401 |
| 6,306,380 B1 | * | 10/2001 | Desmots et al. ................ | 424/73 |
| 6,465,421 B1 | | 10/2002 | Duranton et al. | |
| 6,867,179 B1 | * | 3/2005 | Gilchrest et al. ............... | 514/8.4 |
| 7,531,562 B2 | * | 5/2009 | Fahl et al. ..................... | 514/365 |
| 2002/0155163 A1 | * | 10/2002 | Benjamin et al. ............. | 424/600 |
| 2004/0205910 A1 | | 10/2004 | Li et al. | |
| 2005/0208086 A1 | * | 9/2005 | Commo et al. ............... | 424/401 |
| 2008/0305054 A1 | * | 12/2008 | Vielhaber et al. ............. | 424/59 |

FOREIGN PATENT DOCUMENTS

| | | | |
|---|---|---|---|
| EP | 545147 A2 | * | 6/1993 |
| EP | 0 648 488 A1 | | 4/1995 |
| EP | 0 656 201 A1 | | 6/1995 |
| EP | 1 616 551 A1 | | 1/2006 |
| FR | 2 863 484 A1 | | 6/2005 |
| KR | 10-2004-0072 | * | 8/2004 |
| WO | WO 01/93824 A1 | | 12/2001 |
| WO | WO 03000208 A1 | * | 1/2003 |
| WO | WO 03/059368 A1 | | 7/2003 |
| WO | WO 03/103616 A2 | | 12/2003 |
| WO | WO 2004103334 A1 | * | 12/2004 |
| WO | WO 2005/065633 A1 | | 7/2005 |

OTHER PUBLICATIONS

Kim et al., "Composition for restoring hair or preventing depilation containing 1,2-dithiolthione derivatives", Aug. 18, 2004, Derwent Acc No. 2005-019056, abstract.*
International Search Report issued May 29, 2006 in PCT/FR2005/003196.
French Search Report, issued in corresponding French Application No. FR 0413756, on Sep. 8, 2005.
XP-002343902, Amorepacific Corp., Derwent Publications Ltd., "Composition for restoring hair or preventing depilation containing 1,2-dithiolthione derivative", Aug. 18, 2004.
XP-002343904, Toyo Seito KK, Derwent Publications Ltd., "Peroral hair-nourishing agent—comprising alpha-glucosylated rutin, prevents hair loss and greying", Jan. 6, 1995.
XP-002343903, Alsoa Sogo Kenkyush, Derwent Publications Ltd., "Hair tonic material—contg. one or more of quercetin and its glycoside(s)", Apr. 3, 1991.
XP002378438, John Gray, "The World of Hair", 2003, Procter & Gamble, XP002378438, http://www.pgbeautyscience.com/the-world-of-hair1.html, p. 24.

* cited by examiner

*Primary Examiner* — Gina C Justice

(74) *Attorney, Agent, or Firm* — Buchanan Ingersoll & Rooney PC

(57) ABSTRACT

At least one compound that increases the level of glutathione (GSH) in the melanocytes of hair follicles, and admixtures thereof with other active agents selected from among active agents for combating desquamative conditions of the scalp, plant extracts having propigmenting activity and active agents that slow hair loss and/or promote hair regrowth, are useful for preventing and/or limiting and/or stopping the development of canities.

2 Claims, 2 Drawing Sheets

ADMINISTRATION OF COMPOUNDS THAT INCREASE GLUTATHIONE LEVELS IN THE MELANOCYTES FOR THE TREATMENT OF CANITIES

CROSS-REFERENCE TO PRIORITY/PCT APPLICATIONS

This application claims priority under 35 U.S.C. §119 of FR 0413756, filed Dec. 22, 2004, and is a continuation of PCT/FR 2005/003196, filed Dec. 20, 2005 and designating the United States (published in the French language on Jul. 6, 2006 as WO 2006/070101 A1; the title and abstract were also published in English), each hereby expressly incorporated by reference in its entirety and each assigned to the assignee hereof.

BACKGROUND OF THE INVENTION

1. Technical Field of the Invention

The present invention relates to the cosmetic administration of compounds that increase the level of glutathione (GSH) in the melanocytes of the hair follicle for treating canities.

2. Description of Background and/or Related and/or Prior Art

The hair follicle is a tubular invagination of the epidermis which extends to the deep layers of the dermis. The bottom part, or hair bulb, itself comprises an invagination in which the dermal papilla is located. The bottom part of the bulb is a cell proliferation zone where the precursors of the keratinized cells making up the hair are found. The ascending cells derived from these precursors become gradually keratinized in the top part of the bulb, and this group of keratinized cells will form the hair shaft.

The color of head hair and of body hair depends in particular on the presence, in variable quantities and ratios, of two groups of melanins: eumelanins (brown and black pigments) and pheomelanins (red and yellow pigments). The pigmentation of head hair and of body hair requires the presence of melanocytes in the bulb of the hair follicle. These melanocytes are in an active state, that is to say that they synthesize melanins. These pigments are transmitted to the keratinocytes intended to form the hair shaft, which will result in the growth of a pigmented head hair or body hair. This structure is called hereinafter "follicular unit of pigmentation".

In mammals, melanogenesis involves at least three enzymes: tyrosinase, DOPAchrome tautomerase (TRP-2, for Tyrosinase Related Protein 2) and DHICA oxidase (TRP-1, for Tyrosinase Related Protein 1).

Tyrosinase is the enzyme which initiates the biosynthesis of melanins. It is also described as being the limiting enzyme of melanogenesis.

TRP-2 catalyzes the tautomerization of DOPAchrome to 5,6-dihydroxyindole-2-carboxylic acid (DHICA). In the absence of TRP-2, DOPAchrome undergoes spontaneous decarboxylation to form 5,6-dihydroxyindole (DHI).

DHICA and DHI are both precursors of pigments, TRP-1 oxidizes DHICA molecules to form derivatives of quinones (Pawelek J. M. and Chakraborty A. K., The Enzymology of Melanogenesis. In: Nordlund J. J., Boissy R. E., Hearing V. J., King R. A., Ortonne J. P. The Pigmentary System: *Physiology and Pathophysiology*, New York: Oxford University Press; 1998. p. 391-400).

The three enzymes, tyrosinase, TRP-2 and TRP-1, appear to be specifically involved in melanogenesis. Furthermore, the activity of these three enzymes has been described as being necessary for the maximum activity of biosynthesis of eumelanins.

Head hair and body hair undergo a cycle. This cycle comprises a growth phase (anagen phase), a degenerative phase (catagen phase) and a resting phase (telogen phase) after which a new anagen phase will develop. Because of this hair cycle, and unlike the epidermal pigmentation unit, the follicular unit of pigmentation-must also be cyclically renewed.

Canities (natural graying of the hair) is linked to a specific and gradual depletion of the melanocytes of the hair which affects both the melanocytes of the hair bulb and the precursor cells for melanocytes (Commo et al., *Br. J. Dermatol.,* 2004; 150: 435-443). Other cell types present in the hair follicles are not affected. Furthermore, this depletion of melanocytes is not observed in the epidermis. The cause of this gradual and specific depletion of melanocytes and precursors of melanocytes in the hair follicle has so far not been identified.

It therefore appears to be necessary to combat the disappearance of the melanocytes of the human hair follicles, a process which affects both the active melanocytes of the bulbs and the quiescent melanocytes of the top region of the hair follicles, in order to combat canities.

The assignee hereof has already described a means for combating graying of the hair by action on the enzyme TRP-2 (WO 03/103568).

SUMMARY OF THE INVENTION

Surprisingly and unexpectedly, it has now been determined that the expression of the enzyme TRP-2 is correlated with the expression of GSH; indeed, the expression of TRP-2 induces an increase in the GSH level in the melanocytes.

Thus, it has now been demonstrated that the melanocytes which do not express TRP-2 (for example the precursors of melanocytes of the hair), there is a low GSH level compared with the melanocytes which express the enzyme TRP-2 (for example all the melanocytes of the skin).

Thus, a new target for the treatment of canities has now been identified; it has been demonstrated that the compounds capable of increasing the GSH level in the melanocytes lead, by contrast to their depigmenting effect described in the literature, to the restoration of the pigmentation of the hair.

This application is particularly surprising in nature given that the compounds known for increasing the GSH level in the melanocytes, such as lipoic acid and hydrocoumarins (Yamamura et al. 2002, Lin et al. 2002), are described as agents limiting the synthesis of melanins and thus reducing the pigmentation of the skin in agreement with the demonstration that GSH is unfavorable to the synthesis of melanins (Del Marmol et al. 1993, Jara et al. 1988).

Thus, the present invention features the administration of compounds that increase the level of GSH in the melanocytes of the hair as agents which prevent, limit or stop the progression of canities, and to maintain and/or promote the natural repigmentation of head hair and/or body hair.

In particular, this invention features the administration of a compound that increases the level of GSH for preventing and/or limiting and/or stopping the development of canities.

The compounds capable of increasing the level of GSH are, for example, compounds inducing the synthesis of GSH or, alternatively, compounds limiting its consumption; they can in particular be identified by the following method:

(a) culturing of the melanocytes, for example a primary culture of melanocytes of skin or hair obtained as described in the article by Commo et al; *Pigment Cell Res.,* 2004; 17: 488-497;

(b) addition, to the culture medium, of a compound for which it is desired to test the property of increasing the GSH level;

(c) incubation of the melanocytes for a sufficiently long period in order to allow the compound to be active;

(d) measurement of the GSH level;

(e) selection of the compounds which increase the GSH level.

In a specific embodiment of the method of identifying a compound which increases the GSH level, the cell cultures are carried out in an incubator, at 37° C., 5% $CO_2$.

In particular, step (a) may be carried out according to the following protocol: the melanocytes are inoculated at D0 with M2 medium (PromoCell, Heidelberg, D). This may be for example a primary culture of melanocytes of hair or skin obtained as described in the article by Commo et al., *Pigment Cell Res.*, 2004; 17: 488-497.

The cells are maintained in this culture medium from 12 and 72 hours before the treatment.

Step (b) may be carried out according to the following protocol: the melanocytes are treated in culture with the compound for which it is desired to test the property of increasing the GSH level for the time necessary to reveal this property, this time is generally from 12 and 72 hours.

Step (d) for measuring the GSH level may be carried out, for example, by the HPLC method. In a particular embodiment of this measurement, the free amino acids (AA) extracted from cultured and treated cells are analyzed with the aid of an automatic HITACHI L-8500 amino acid analyzer. In this way, the free amino acids are separated on an ion-exchange column with eluents based on lithium salts, and then assayed by colorimetry after reaction with ninhydrin.

The GSH assay may also be carried out by a fluorescence method with the aid of an intracellular fluorescent GSH probe, for example such as monochlorobimane (Molecular Probes, USA).

Alternatively, the GSH assay may be carried out with the aid of commercial kits such as the Bioxytech GSH-400 calorimetric assay kit (Calbiochem, USA).

The present invention also features administration of a compound that increases the GSH level in order to maintain the natural pigmentation of grey head hair and/or body hair.

The compound that increases the GSH level may be selected in particular from lipoic acid, oltipraz, kahweol, cafestol, angelicalactone, diallyl sulfide and benzyl isothiocyanate (Scharf G et al., *Nutr Cancer.*, 2003; 45(1): 74-83, Huber W W et al., *Environ Mol Mutagen.*, 2004; 44(4): 265-276, Sheen L Y et al., *Food Chem Toxicol.*, 1996; 34(10): 971-978, Gupta E et al., *Clin. Cancer Res.*, 1995; 1(10): 1133-1138).

Preferably, the compound that increases the GSH level will not be N-acetylcysteine or quercitin.

This invention also features compositions for combating canities, comprising formatted into a cosmetically acceptable medium, at least one compound that increases the level of GSH as defined above, notably with the exception of N-acetylcysteine and quercitin, combined with another active agent selected from agents for combating the desquamative of the scalp and/or plant extracts with propigmenting activity.

Preferably, the compound that increases the GSH level is selected from lipoic acid, oltipraz, kahweol, cafestol, angelicalactone, diallyl sulfide and benzyl isothiocyanate.

The present invention also features compositions for combating canities, comprising, formulated into a cosmetically acceptable medium, at least one compound that increases the level of GSH selected from oltipraz, kahweol, cafestol, angelicalactone and benzyl isothiocyanate, combined with an agent for promoting hair regrowth.

Figure 1:
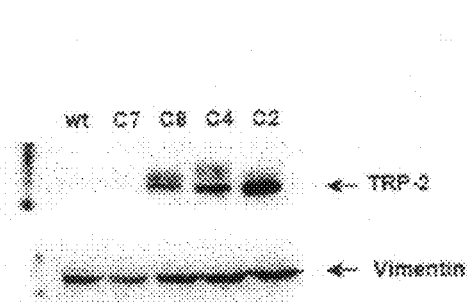
FIG. 1 is Western blot with anti-TRP-2 and anti-vimentin antibodies on the melanocyte lines WM35-wt (wild type), C2, C4, C7 and C8 (transfected and selected clones) as described in Example 1; it is evident from this Western blot that only clones C2, C4 and C8 express TRP-2.

DETAILED DESCRIPTION OF BEST MODE AND SPECIFIC/PREFERRED EMBODIMENTS OF THE INVENTION

The compositions according to the invention comprise a quantity of compound capable of increasing the GSH level of from 0.001% to 10% by weight per volume, preferably from 0.01% to 5% by weight per volume and more preferably still from 0.1% to 1% by weight per volume.

The compositions according to the invention may be administered orally or may be applied topically to the skin (over any skin area of the area covered with body hair) and/or the scalp.

Orally, the compositions according to the invention may contain the compound(s) that increase the GSH level in solution in a dietary fluid such as an optionally flavored aqueous or aqueous-alcoholic solution. They may also be incorporated into an ingestible solid excipient and may be provided, for example, in the form of granules, pills, tablets or sugar-coated tablets. They may also be placed in solution in a dietary fluid which is itself optionally packaged in ingestible capsules.

Depending on the mode of administration, whether regime or regimen, the compositions of the invention may be provided in any galenic forms normally used, particularly in cosmetology.

A preferred composition of the invention is a cosmetic composition suitable for topical application to the scalp and/or the skin.

For a topical application, the composition according to the invention may be in particular in the form of an aqueous, aqueous-alcoholic or oily solution or of a dispersion of the lotion or serum type, of emulsions of liquid or semiliquid consistency of the milk type, which are obtained by dispersing a fatty phase in an aqueous phase (O/W) or conversely (W/O), or of suspensions or emulsions of a soft consistency of the cream or aqueous gel or anhydrous type, or alternatively of microcapsules or microparticles, or of vesicular dispersions of the ionic and/or non-ionic type. It may thus be provided in the form of a salve, a tincture, a cream, an ointment, a powder, a patch, an impregnated pad, a solution, an emulsion or a vesicular dispersion, a lotion, a gel, a spray, a suspension, a shampoo, an aerosol or a foam. They may be anhydrous or aqueous. It may also consist of solid preparations constituting soaps or glazing cakes.

These compositions are formulated according to the customary methods.

The composition that is administered according to the invention may be in particular a composition for hair care, and in particular a shampoo, a hair-setting lotion, a treatment lotion, a hair-styling cream or gel, a dyeing (in particular oxidation dyeing) composition optionally in the form of dyeing shampoos, restructuring lotions for the hair, or a mask.

The cosmetic composition according to the invention will preferably be a cream, a hair lotion, a shampoo or a conditioner.

The quantities of the various constituents of the compositions that are administered according to the invention are those conventionally used in the fields in question.

When the composition according to the invention is an emulsion, the proportion of the fatty phase may range from 5% to 80% by weight, and preferably from 5% to 50% by weight relative to the total weight of the composition. The oils, waxes, emulsifiers and coemulsifiers used in the composition in the form of an emulsion are selected from those conventionally used in the cosmetic field. The emulsifier and coemulsifier included in the composition in a proportion ranging from 0.3% to 30% by weight, and preferably from 0.5% to 20% by weight relative to the total weight of the composition. The emulsion may additionally contain lipid vesicles.

When the composition according to the invention is an oily gel or solution, the fatty phase may represent more than 90% of the total weight of the composition.

In one embodiment of the invention, the composition will be such that the compound capable of increasing the GSH level is encapsulated in a coating such as microspheres, nanospheres, oleosomes or nanocapsules, the coating will be selected according to the chemical nature of the compound capable of increasing the GSH level.

By way of example, the microspheres may be prepared according to the method described in EP-0-375,520.

The nanospheres can be provided in the form of an aqueous suspension and can be prepared according to the methods described in FR-0015686 and FR-0101438.

Oleosomes consist of an oil-in-water emulsion formed by oily globules provided with a lamellar liquid crystal coating dispersed in an aqueous phase (see EP-0-641,557 and EP-0-705,593).

The compounds that increase the GSH level may also be encapsulated in nanocapsules consisting of a lamellar coating obtained from a silicone surfactant (see EP-0-780,115), the nanocapsules can also be prepared based on water-dispersible sulfonic polyesters (see FR-01 13337).

The compounds that increase the GSH level may also form a complex at the surface of cationic oily globules regardless of their size (see EP-1-010,413, EP-1-010,414, EP-1-010,415, EP-1-010,416, EP-1-013,338, EP-1-016,453, EP-1-018,363, EP-1-020,219, EP-1-025,898, EP-1-120,101, EP-1-120,102, EP-1-129,684, EP-1-160,005 and EP-1-172,077).

The compounds that increase the GSH level may finally form a complex at the surface of nanocapsules or nanoparticles provided with a lamellar coating (see EP-0-447,318 and EP-0-557,489) and containing a cationic surfactant at the surface (see the references cited above for cationic surfactants).

In particular, a composition will be preferred such that the coating containing the compound capable of increasing the GSH level has a diameter less than or equal to 10 µm. When the coating does not form a spherical vesicle, the term diameter means the largest dimension of the vesicle.

In a known manner, the compositions according to the invention may also contain customary adjuvants in the cosmetic field, such as hydrophilic or lipophilic gelling agents, hydrophilic or lipophilic additives, preservatives, antioxidants, solvents, perfumes, fillers, screening agents, odor absorbers and coloring matter. The quantities of these various adjuvants are those conventionally used in the cosmetic field, and are for example from 0.01% to 10% of the total weight of the composition. These adjuvants, depending on their nature, may be introduced into the fatty phase, into the aqueous phase and/or into the lipid spherules.

As oils or waxes which can be used in the invention, exemplary are mineral oils (liquid paraffin), vegetable oils (liquid fraction of shea butter, sunflower oil), animal oils (perhydrosqualene), synthetic oils (Purcellin oil), silicone oils or waxes (cyclomethicone) and fluorinated oils (perfluoropolyethers), beeswax, carnauba wax or paraffin wax. It is also possible to add to these oils fatty alcohols and fatty acids (stearic acid).

As emulsifiers which can be used in the invention, exemplary are glyceryl stearate, polysorbate 60 and the PEG-6/PEG-32/glycol stearate mixture marketed under the trademark Tefose® 63 by the company Gattefosse.

As solvents which can be used in the invention, exemplary are lower alcohols, in particular ethanol and isopropanol, propylene glycol.

As hydrophilic gelling agents which can be used in the invention, exemplary are carboxyvinyl polymers (carbomer), acrylic copolymers such as acrylate/alkyl acrylate copolymers, polyacrylamides, polysaccharides such as hydroxypropylcellulose, natural gums and clays, and, as lipophilic gelling agents, exemplary are modified clays such as bentones, metal salts of fatty acids such as aluminum stearates and hydrophobic silica, ethylcellulose, polyethylene.

The compositions according to the invention may combine at least one compound capable of increasing the GSH level with other active agents. Among these active agents, exemplary are:

agents modulating the differentiation and/or proliferation and/or pigmentation of skin cells such as retinol and its esters, vitamin D and its derivatives, oestrogens such as oestradiol, cAMP modulators such as the POMC derivatives, adenosine or forskolin and its derivatives, prostaglandins and derivatives thereof, triiodothrionine and its derivatives;

plant extracts such as those of Iridaceae or of soybean, which extracts may or may not then contain isoflavones;

extracts of microorganisms;

anti-free radical agents such as α-tocopherol or its esters, superoxide dismutases or its mimetics, certain metal chelators or ascorbic acid and its esters;

anti-seborrhoeics such as certain sulfur-containing amino acids, 13-cis-retinoic acid, cyproterone acetate;

other agents for combating the desquamative states of the scalp such as zinc pyrithione, selenium disulfide, climbazole, undecylenic acid, ketoconazole, piroctone olamine (octopirox) or ciclopiroctone (ciclopirox);

in particular, there may be active agents stimulating hair regrowth and/or promoting the slowing of hair loss, and more particularly exemplary are:

esters of nicotinic acid, including in particular tocopheryl nicotinate, benzyl nicotinate and $C_1$-$C_6$ alkyl nicotinates such as methyl or hexyl nicotinates;

derivatives of pyrimidine, such as 2,4-diamino-6-piperidinopyrimidine 3-oxide or "Minoxidil" described in U.S. Pat. Nos. 4,139,619 and 4,596,812; Aminexil or 2,4-diaminopyrimidine 3-oxide described in WO 96/09048;

lipoxygenase inhibiting agents or cyclooxidase inducing agents promoting hair regrowth such as those described by the assignee hereof in EP-0-648,488;

antibacterial agents such as macrolides, pyranosides and tetracyclines, and in particular erythromycin;

calcium antagonists, such as cinnarizine, nimodipine and nifedipine;

hormones, such as oestriol or analogues, or thyroxine and its salts;

anti-androgen agents such as oxendolone, spironolactone, diethylstilbestrol and flutamide;

steroid or non-steroid inhibitors of 5-α-reductases, such as those described by the assignee hereof in EP-0-964,852 and EP-1-068,858 or alternatively finasteride;

ATP-dependent potassium channel agonists such as cromakalim and nicorandil;

plant extracts with propigmenting activity such as chrysanthemum extracts as described in FR-2768343 and Sanguisorba extracts described in FR-2782920A1.

Preferably, the compound that increases the GSH level is combined with another active agent selected from agents for combating the desquamative conditions of the scalp, agents promoting hair regrowth, and plant extracts with propigmenting activity.

The present invention also features a regime or regimen for the cosmetic treatment of canities, wherein a composition as defined above, comprising at least one compound that increases the GSH level, is administered or topically applied to the area to be treated.

This invention also relates to a method of cosmetic treatment useful to maintain the natural pigmentation of grey or white head hair and/or body hair, wherein a composition as defined above, comprising at least one compound capable of increasing the GSH level, is topically applied to the area to be treated.

The methods for treating canities and pigmentation of grey or white head hair and/or body hair may also entail ingesting a composition comprising at least one compound capable of increasing the GSH level.

The areas to be treated may be, for example and with no limitation, the scalp, the eyebrows, the moustache and/or the beard and any area of the skin that is covered with hair.

More particularly, the methods for the cosmetic treatment of canities and the natural pigmentation of grey or white head hair and/or body hair entail applying a composition comprising at least one compound capable of increasing the GSH level.

The methods of cosmetic treatment for combating canities and/or for maintaining the natural pigmentation of grey or white head hair and/or body hair may for example entail applying the composition to the hair and the scalp, in the evening, keeping the composition overnight and optionally rinsing in the morning or washing the hair with the aid of this composition and again leaving it in contact for a few minutes before rinsing. The compositions in accordance with the invention have proved particularly advantageous when they are applied in the form of an optionally rinse-out hair lotion or even in the form of a shampoo.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Assay of GSH in Melanocytes as a Function of the Expression of TRP-2

A: Production of TRP-2 positive and TRP-2 negative melanocyte lines:

A1: Cloning of the TRP-2 protein:

The entire region of the messenger RNA encoding the TRP-2 protein is cloned, from messenger RNAs extracted from a primary culture of skin melanocytes, by the RT-PCR technique with the aid of the probes 5'-GGAGATGGT-GAGAAGCGCTAC-3' (SEQ ID NO:1) and 5'-GCG-GAAACTACAGCTAAGCAT-3' (SEQ ID NO:2), according to the Genebank D17547 sequence. The PCR product obtained is again cloned with the aid of probes containing nucleotide sequences corresponding to the restriction sites for cloning into an eukaryotic expression vector:

5'-AGGGATCCATGAGCCCCCTTTGGTGGGGGTTT-3' (SEQ ID NO:3) and 5'-GGAATTCAGCACCCTAG-GCTTC-3' (SEQ ID NO:4). The expression vector used is pCDNA3.1(+). The vector containing the region encoding the TRP-2 protein is then produced from competent bacteria and then purified, this vector is then called pCDNA-TRP2.

A2: Production of TRP-2 positive melanoma lines:

Cells of the melanoma type WM35 (Pak B J et al. Melanoma Res. 2000; 10: 499) which weakly express the TRP-2 protein constitutively in vitro (wild-type line) are transfected with the plasmid pCDNA-TRP2. The stably transfected cells are then selected by treatment with geneticin (G418). The clones obtained are then isolated and amplified.

B: Verification of the differential expression of TRP-2 in the various clones selected, by the Western blot method (see Commo et al; Pigment Cell Res 2004; 17: 488-497)

Cultures of each of the clones are lysed with the same lysis buffer appropriate for protein extraction and Western blot analysis. The TRP-2 level in the various extracts is determined by the Western blot method from 8 μg of protein extracts. The Western blot (see protocol in Maniatis et al.) is produced with the following antibodies:

αPEP8h, a polyclonal antibody given by Dr V J Hearing (NIH, Bethesda, USA), and xvimentin, a monoclonal antibody Vim3B4 (Cymbus, UK).

FIG. 1 shows that the clones C2, C4 and C8 express the TRP-2 protein more compared with clone 7 and the wild-type (wt) line.

C: Assay of GSH in the TRP-2 positive and TRP-2 negative clones

For each of the clones studied, the cells are inoculated at the rate of $2 \times 10^4$ cells/cm$^2$. The cell cultures are then lysed with the aid of a lysis buffer pH 2. The free amino acids (AA) extracted are analyzed with the aid of the automatic HITACHI L-8500 amino acid analyzer. In this way, the free AAs are separated on an ion-exchange column with eluents based on lithium salts, and then assayed by colorimetry after reaction with ninhydrin. In each extract, the GSH level measured is expressed relative to the sum of the AAs (proline (P), glycine (G), alanine (A), valine (V), cysteine (C), methionine (M), isoleucine (I), leucine (L), tyrosine (Y), phenylalanine (F), lysine (K), histidine (H), arginine (R)) so as to normalize the sample.

Figure 2:
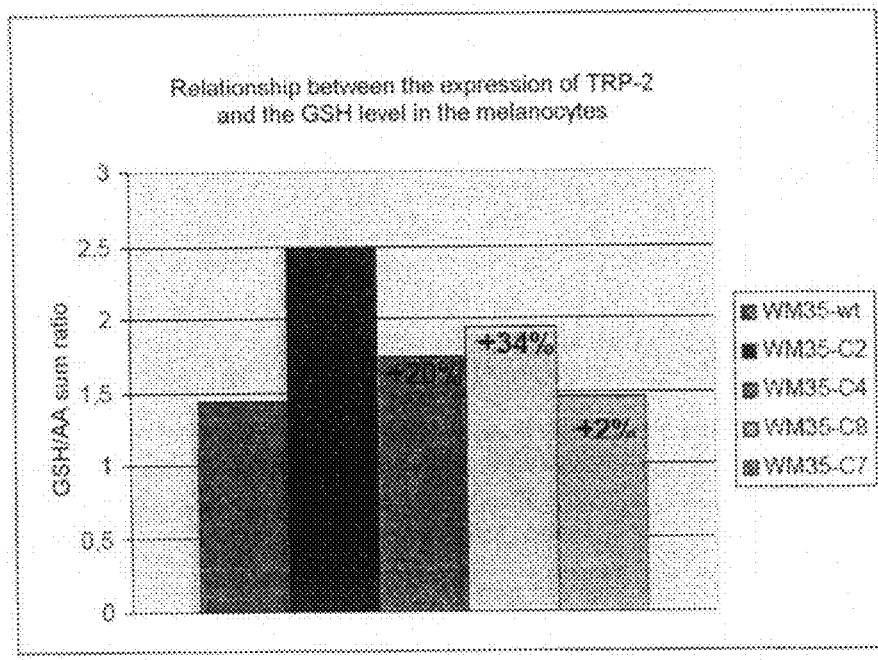
FIG. 2 is a histogram representing the ratio of GSH over the sum of a selection of amino acids assayed (see Example 1, part C) in the melanocyte lines WM35-wt (wild type), C2, C4, C7 and C8.

FIG. 2 shows that the clones C2, C4 and C8 possess a higher GSH level than clone C7 and than the wild-type line.

Example 2

Example of the Effect of Compounds which Increase the GSH Level or Limit its Reduction on the Viability of the TRP-2(−) melanocytes The principle of this assay is the following:

a: culturing of two cell types expressing TRP-2 and not expressing TRP-2, developed according to a method similar to that used in Example 1A, TRP-2(+) cell and TRP2(−) cell respectively; these may be any type of cells, preferably melanocytes.

b: addition to the TRP2(−) cell culture medium of a compound capable of promoting the accumulation of GSH.

c: incubation of the cultures for a sufficiently long period to allow an increase in the GSH level in the cells.

d: exposure of the cells to a condition inducing apoptosis or senescence.

e: measurement of apoptosis or senescence.

f: selection of the compounds promoting the accumulation of GSH and making it possible to protect the TRP2(−) cells.

In a particular embodiment of the method, the cell cultures are performed in an incubator, at 37° C., 5% $CO_2$.

In particular, step (a) may be performed according to the following protocol: the cells are inoculated at the density of $5 \times 10^4$ cells/cm$^2$, on D0 with M2 medium (PromoCell, Heidelberg, D). The cells are maintained in this culture medium from 12 and 72 hours before the treatment.

Step (b) may be performed according to the following protocol: the cells are treated in culture with the test compound for the time necessary to reveal this property, this time is generally from 12 and 72 hours.

To carry out step (d), the TRP2(+) cell and TRP2(−) cell populations are exposed to a condition inducing apoptosis or senescence in culture; this may be, for example, a treatment with cisplatin (Pak B. J. et al., 2000, *Melanoma Res.*, 10: 499-505) or oxaliplatin, with a toxic agent or a precursor compound for toxic molecules such as adriamycin, dihydroxyphenylalanine, paraquat, paracetamol, 4-hydroxyoestradiol, or alternatively 4-hydroxyanisol, an exposure to ultraviolet rays, an oxidative stress ($H_2O_2$, diethyl maleate) (see Vaux D. L. & Strasser A., 1996, *Proc. Natl. Acad. Sci.*, 93: 2239-2244).

To carry out step (e), it will be possible to use the following methods for revealing apoptosis or senescence:

the apoptotic response may be determined by any method allowing cell apoptosis to be revealed, for example identification of the fragmentation of DNA after electrophoresis on agarose gel, labeling of the DNA fragments by the "TUNNEL" method (Gavrieli Y et al. *J Cell Biol.*, 1992; 119: 493-501), revealing of anexin V (ApoAlert Annexin V Apoptosis Kit (1996) CLONTECHniques XI(3): 9-11 (BD Biosciences, Belgium)), assay of cytosolic nucleosomes (Kit Cell Death Detection ElisaPlus (1-774-425, Roche, Germany)); measurement of cell viability.

the senescent response may be determined by any method allowing cellular senescence to be revealed, for example determination of a shortening of the telomeres, measurement of the activity of telomerase (TRAPeze kit, Intergen), determination of the reduction of the level of cycline E, determination of the reduction of the level of phosphorylated protein Rb (Bandyopadhyay D et al. *Experimental Gerontology* 2001; 36: 1265-1275), measurement of the beta-galactosidase activity (Dimri G P et al. *PNAS* 1995; 92: 9363-9367).

In the present case, the measurement was carried out of the capacity, on the one hand, of the cafestol/kahweol mixture and, on the other hand, of oltipraz to compensate for the weak expression of TRP-2 in the wild-type line WM35 by protecting this cell line when these cells are exposed to an $H_2O_2$ stress.

The study was carried out with the aid of the human melanocyte line WM35, which very weakly expresses TRP-2 (Pak B J et al. Melanoma Res. 2000; 10: 499), called the "wild-type" line in the study and a cell line derived from the WM35 line which highly expresses TRP-2, called "clone-2" in the study, obtained by transfection (see points A and B of Example 1).

To carry out the test, the cells are inoculated at the density of $2.5 \times 10^4$ cells/well and then treated with the compounds to be evaluated:

a—1:1 mixture containing 4 μg/ml of cafestol and kahweol;

b—oltipraz at 50 μM.

After 24 h, the cells are exposed to a stress induced by $H_2O_2$.

The cell viability is measured 24 h after the stress with the aid of 2',7'-dichlorodihydrofluoresceine diacetate ($H_2DCFDA$; D399, Molecular Probes).

Figure 3:
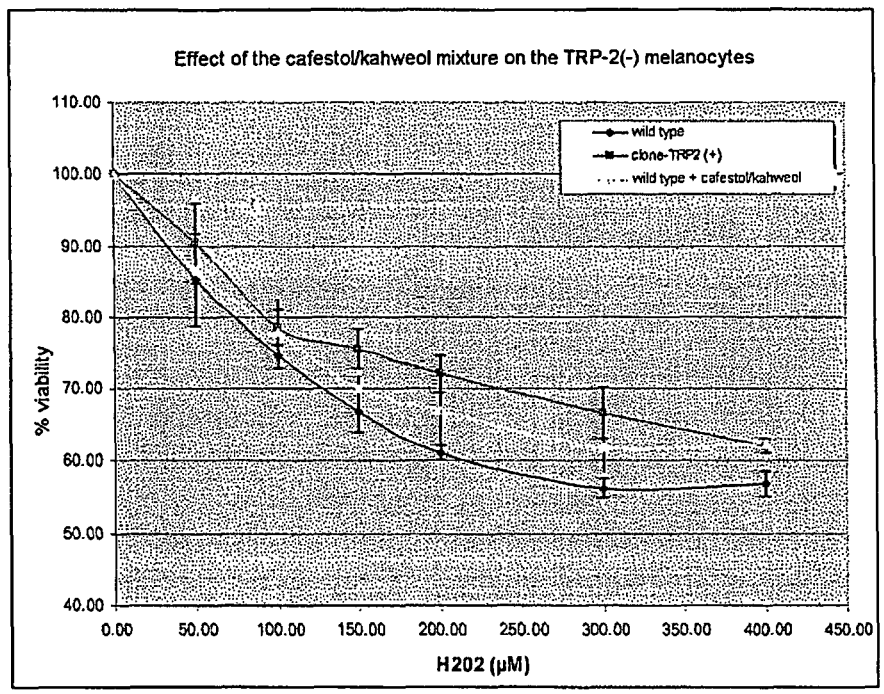
FIGS. 3 and 4 represent the effect of an oxidative stress ($H_2O_2$) on the cellular viability of wild-type melanocytes weakly expressing or not expressing TRP-2 (diamond) melanocytes TRP2(+) (square) and wild-type melanocytes weakly expressing or not expressing TRP-2 treated with the combination of cafestol+kahweol (FIG. 3) or with oltipraz (FIG. 4) (triangle).
Figure 4:
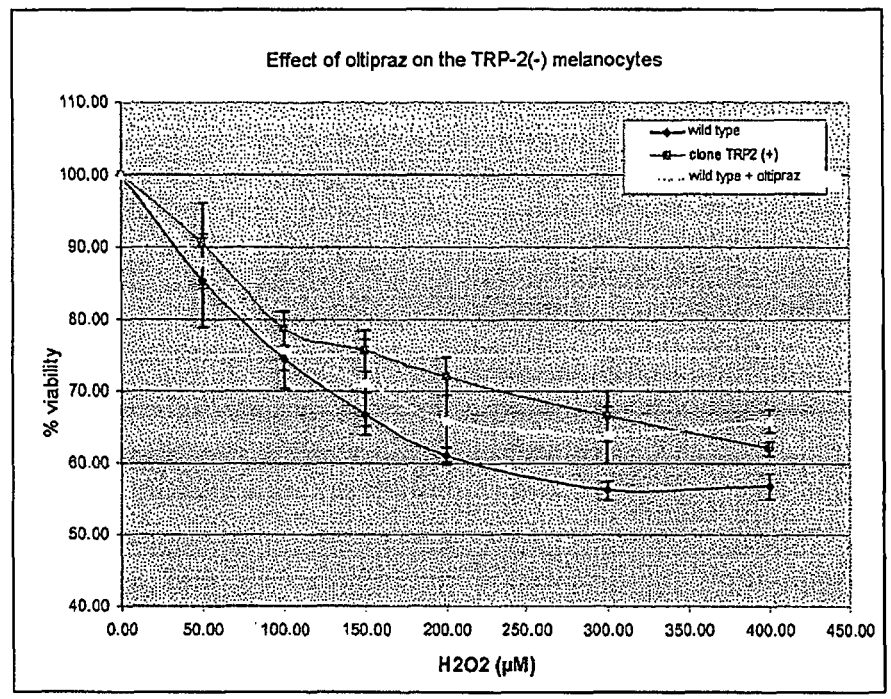

The results obtained (Tables 1 and 2 and FIGS. 3 and 4) show that the treatment of the wild-type line, on the one hand, with a cafestol/kahweol mixture and, on the other hand, with oltipraz limits the sensitivity of the cells to $H_2O_2$ induced stress. The results thus show that after the treatment, the sensitivity of the wild-type line becomes comparable to the sensitivity of the clone-2 line.

TABLE 1

Cafestol + kahweol treatment (the results are expressed in % viability as a function of the $H_2O_2$ treatment):

| | $H_2O_2$ (in μM) | | | | | | |
|---|---|---|---|---|---|---|---|
| | 0 | 50 | 100 | 150 | 200 | 300 | 400 |
| Wild-type | 100.00 +/− 0 | 85.25 +/− 6.44 | 74.58 +/− 1.68 | 66.87 +/− 2.96 | 61.15 +/− 0.97 | 56.23 +/− 1.32 | 56.88 +/− 1.81 |
| Wild-type + cafestol/kahweol | 100.00 +/− 0 | 86.47 +/− 4.79 | 77.84 +/− 4.63 | 69.95 +/− 1.87 | 66.95 +/− 4.69 | 61.87 +/− 3.43 | 62.36 +/− 0.97 |
| Clone 2 | 100.00 +/− 0 | 90.40 +/− 5.63 | 78.60 +/− 2.48 | 75.60 +/− 2.82 | 72.11 +/− 2.62 | 66.61 +/− 3.54 | 62.12 +/− 0.97 |

TABLE 2

Oltipraz treatment (the results are expressed in % viability as a function of the H₂O₂ treatment):

| | $H_2O_2$ (in µM) | | | | | | |
|---|---|---|---|---|---|---|---|
| | 0 | 50 | 100 | 150 | 200 | 300 | 400 |
| Wild-type | 100.00 +/− 0 | 85.25 +/− 6.44 | 74.58 +/− 1.68 | 66.87 +/− 2.96 | 61.15 +/− 0.97 | 56.23 +/− 1.32 | 56.88 +/− 1.81 |
| Wild-type + cafestol/kahweol | 100.00 +/− 0 | 86.47 +/− 3.52 | 77.84 +/− 5.44 | 69.95 +/− 6.0 | 66.95 +/− 5.98 | 61.87 +/− 3.94 | 62.36 +/− 1.61 |
| Clone 2 | 100.00 +/− 0 | 90.40 +/− 5.63 | 78.60 +/− 2.48 | 75.60 +/− 2.82 | 72.11 +/− 2.62 | 66.61 +/− 3.54 | 62.12 +/− 0.97 |

It can be concluded that the treatment of the melanocytes weakly expressing or not expressing TRP-2, on the one hand, with a cafestol/kahweol mixture and, on the other hand, with oltipraz compensates for the weak expression of TRP-2 in terms of the sensitivity to $H_2O_2$ induced stress and is thus beneficial to the melanocytes having a weak or zero TRP-2 expression level.

Example 3

Compositions

Hair Lotion:

| | |
|---|---|
| Compound capable of acting on the metabolic pathway of DOPAchrome tautomerase | 0.5 g |
| Propylene glycol | 20 g |
| Ethanol, 95% | 30 g |
| Water | qs 100 g |

This lotion is applied daily to the areas to be treated and preferably to the entirety of the scalp for at least 10 days and preferably for 1 to 2 months.

A reduction in the appearance of white or grey hair and a repigmentation of grey hair are observed in this case.

Treatment Shampoo:

| | |
|---|---|
| Compound capable of acting on the metabolic pathway of DOPAchrome tautomerase | 1.5 g |
| Polyglyceryl 3-hydroxylaryl ether | 26 g |
| Hydroxypropylcellulose marketed under the trademark Klucell G by the company Hercules | 2 g |
| Preservatives | qs |
| Ethanol, 95% | 50 g |
| Water | qs 100 g |

This shampoo is used at each washing with a leave-in time of about one minute. A prolonged use, on the order of two months, results in the gradual repigmentation of grey hair.

This shampoo may also be used preventively in order to delay the graying of hair.

Treatment Gel:

| | |
|---|---|
| Compound capable of acting on the metabolic pathway of DOPAchrome tautomerase | 0.75 g |
| Eucalyptus essential oils | 1 g |
| Econazole | 0.2 g |
| Lauryl polyglyceryl 6 cetearyl glycoether | 1.9 g |
| Preservatives | qs |
| Carbopol 934P marketed by the company B F Goodrich Corporation | 0.3 g |
| Neutralizing agent | qs pH 7 |
| Water | qs 100 g |

This gel is applied to the areas to be treated twice per day (morning and evening) with a final massage. After three months of application, repigmentation of body hair or head hair in the treated area is observed.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

---

What is claimed is:

1. A regime or regimen for limiting the development of canities in a subject in need of such treatment, comprising orally administering thereto an effective amount of at least one compound selected from the group consisting of oltipraz, kahweol, cafestol, angelicalactone, benzyl isothiocyanate, and mixtures thereof, wherein said compound(s) increase(s) the level of glutathione (GSH) in the melanocytes of hair follicles of said subject,
    wherein said compound is encapsulated in a coating of microspheres, nanospheres, oleosomes, or nanocapsules,
    wherein the subject has grey or white head hair and/or body hair, and
    wherein the effective amount is an amount ranging from 0.001% to 10% by weight per volume.

2. A regime or regimen for restoring the natural pigmentation of grey head hair and/or body hair in a subject in need of such treatment, comprising orally administering thereto an effective amount of at least one compound selected from the group consisting of oltipraz, kahweol, cafestol, angelicalactone, diallyl sulfide, benzyl isothiocyanate, and mixtures thereof, wherein said compound(s) increase(s) the level of glutathione (GSH) in the melanocytes of hair follicles of said subject,
    wherein said compound is encapsulated in a coating of microspheres, nanospheres, oleosomes, or nanocapsules,
    wherein the subject has grey or white head hair and/or body hair, and
    wherein the effective amount is an amount ranging from 0.001% to 10% by weight per volume.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 1
ggagatggtg agaagcgcta c                    21

-continued

```
<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
gcggaaacta cagctaagca t                                              21

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
agggatccat gagcccctt tggtgggggt tt                                   32

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
ggaattcagc accctaggct tc                                             22
```